United States Patent [19]

Rinehart, Jr. et al.

[11] 4,075,339

[45] Feb. 21, 1978

[54] BIOLOGICALLY ACTIVE COMPOUNDS

[75] Inventors: Kenneth L. Rinehart, Jr., Urbana, Ill.; Moses W. McMillan, Indianapolis, Ind.; Wojciech Sobiczewski, Warsaw, Poland

[73] Assignee: University of Illinois Foundation, Urbana, Ill.

[21] Appl. No.: 710,575

[22] Filed: Aug. 2, 1976

Related U.S. Application Data

[62] Division of Ser. No. 458,139, April 5, 1974, Pat. No. 3,987,035.

[51] Int. Cl.[2] .................. C07D 487/04; A61K 31/395

[52] U.S. Cl. .................................... 424/250; 424/244; 424/248.54; 260/239.3 B; 260/239.3 P; 260/243.3

[58] Field of Search .................. 260/239.3 P; 424/250

*Primary Examiner*—Henry R. Jiles
*Assistant Examiner*—Robert T. Bond
*Attorney, Agent, or Firm*—Merriam, Marshall & Bicknell

[57] ABSTRACT

Compounds possessing anti-bacterial and anti-viral activity of the formula II,

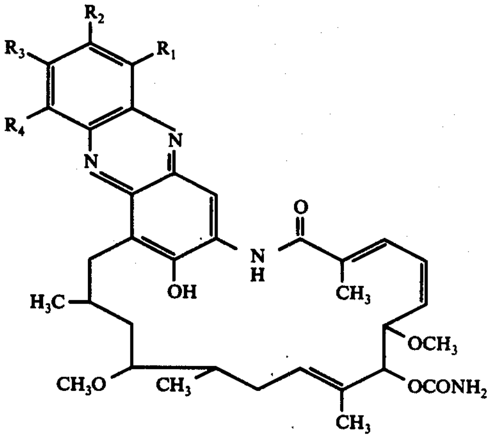

wherein $R_1$, $R_2$, $R_3$, and $R_4$ are the same or different and selected from hydrogen, hydroxy, halo, amino, and $C_1$ to $C_{20}$ alkyl, alkoxyl, alkoxycarbonyl, amide or N-alkyl substituted amide.

3 Claims, No Drawings

BIOLOGICALLY ACTIVE COMPOUNDS

RELATED APPLICATION

This application is a division of application Ser. No. 458,139, filed Apr. 5, 1974 now U.S. Pat. No. 3,987,035.

BACKGROUND

Geldanamycin is a biologically active ansa ring compound derived from *Streptomyces hygroscopicus*, var. *Geldanus*, var. *nova*, [DeBoer, et al., *J.Antibiot.*, 23, 442 (1970) and see, generally, Rinehart, *Accounts Chem. Res.*, 5, 57 (1972)], having a structure as set out below.

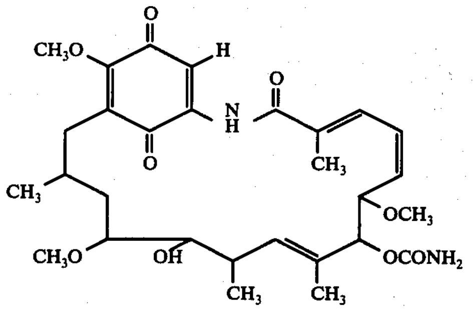

BRIEF DESCRIPTION

The present invention relates to biologically active derivatives of geldanamycin developed generally by: (1) a Mannich reaction of geldanamycin to form imine products of the type of Formula I, (I)

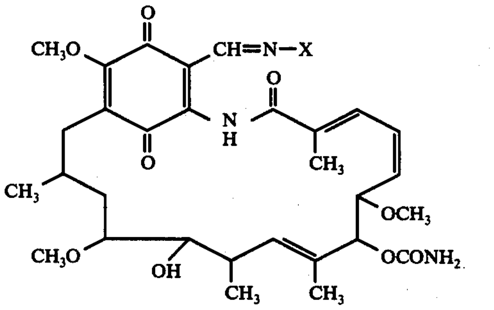

wherein X is $C_1$ to $C_{20}$ alkyl, aryl, aralkyl, alkylamino, aralkylamino, cyclic amino, amido, carboxyl, alkoxyl, or aralkoxyl; (2) reaction of geldanamycin with a suitable O-phenylenediamine directly or reaction with a suitable hydroxide followed by reaction with a suitable O-phenylenediamine to form products of the type of Formula II, (II)

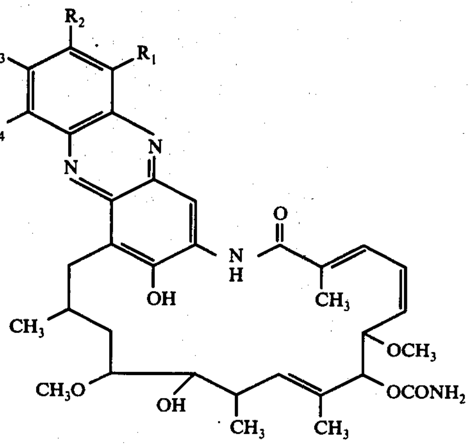

wherein $R_1$, $R_2$, $R_3$, and $R_4$ are the same or different and selected from hydrogen, hydroxy, halo, $C_1$ to $C_{20}$ alkyl, alkoxyl, carboxyl, alkoxycarbamyl, amino, amido, or N-alkyl-substituted amido; or (3) by reaction of geldanamycin with a suitable phenolic amine directly or reaction with a suitable hydroxide followed by reaction with a suitable phenolic amine to form products of the type of Formula III, (III)

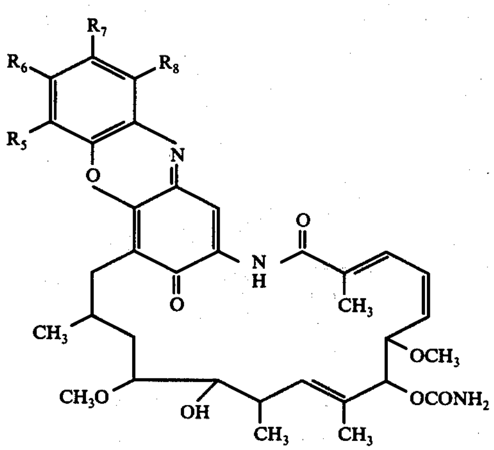

wherein $R_5$, $R_6$, $R_7$ and $R_8$ are the same or different and selected from hydrogen, hydroxy, halo, $C_1$ to $C_{20}$ alkyl, alkoxyl, carboxyl, alkoxycarbonyl, amino, amido, or N-alkyl-substituted amido. It relates also to new pharmaceutical compositions including such compounds and to new therapeutic methods including administration of such compositions. See, generally the 1974 doctoral thesis of Moses W. McMillan, *Studies On the Antibiotic Geldanamycin And Biologically Active Derivatives And Analogues*, The University of Illinois, Urbana-Champaign, Illinois.

DETAILED DESCRIPTION

Compounds of Formula I may be prepared according to the methods of the following Examples which illustrate the preparation of exemplary compounds of that Formula.

EXAMPLE I (1) 0.25 g. of geldanamycin (0.45 mmole) was suspended in 5 ml. of tetrahydrofuran and 0.142 ml. (1.35 mmole) of t-butylamine, and 0.8 ml. (0.95 mmole) of 37% formaldehyde was added. The reaction mixture was heated, with stirring, for 16 hours at 45°-50° C. The solvent was then evaporated to dryness, the residue was dissolved in 5 ml. of benzene and the solvent was evaporated to dryness once more to remove moisture. The residue was dissolved in 5 ml. of benzene and 0.35 g. of manganese dioxide [prepared by the procedure of Mancera, et al., *J. Chem. Soc.*, 2190 (1953)] was added. The mixture was stirred at 45°-50° C. for 1.5 hours, excess manganese dioxide was filtered, and the filtrate was evaporated to dryness. The crude product was dissolved in about 1 ml. of acetone and chromatographed on a silica gel plate with chloroform:methanol:benzene (8:1:1). The large yellow-brown spot was eluted from the silica gel with acetone and the solvent was evaporated to dryness very slowly; the crystalline product was dried under vacuum at 60° C. for 6 hours and yielded 0.166 g. (58%) of product, m.p. 116°-119° C.

Anal. Calcd. for $C_{34}H_{49}N_3O_9$: C, 63.43; H, 7.67; N, 6.52; Found: C, 63.25; H, 7.71; N, 6.59;

(2) A mixture of 2.5 g. (4.5 mmole) of geldanamycin, 50 ml. of tetrahydrofuran, 1.42 ml. (13.5 mmole) of t-butylamine, and 0.8 ml. (9.5 mmole) of 37% formaldehyde was stirred for 16 hr. at 45°-50° C., then evaporated to dryness. The residue was dissolved in 50 ml. of benzene and solvent was evaporated to dryness again to remove moisture, then the residue, 50 ml. of benzene and 3.5 g. of manganese dioxide (as above prepared), was stirred at 45°-50° C. for 1.5 hour. Excess manganese dioxide was filtered and the filtrate was evaporated to dryness. The crude product was dissolved in a small amount of acetone and chromatographed on a silica gel column (4 cm. × 40 cm., containing 196 g. of silica gel) with chloroform:methanol:benzene (8:1:1) as solvent. After elution the second yellow-brown fraction was filtered and the solvent was evaporated to dryness slowly; the yellow-brown product was dried under vacuum at 60° C. for 6 hours.

EXAMPLE II (1) A mixture of 0.167 g. (0.26 mmole) of the product of Example I, 5 ml. of dry ethyl acetate, and 0.043 g. (0.374 mmole) of 4-methyl-1-aminopiperazine was stirred for 6 hours at 60° C. then evaporated to dryness. The crude residue was dissolved in a small amount of acetone and chromatographed on a silica gel plate with chloroform:methanol:benzene (8:1:1) as solvent system. The large purple spot was scraped from the plate and eluted with acetone. Evaporation to dryness gave small purple crystals which were dried under vacuum at 60° for 6 hours to yield 0.074 g. of product (42%), m.p. 135°-138° C.

Analysis calcd. for $C_{35}H_{51}N_5O_9$: C,61.29; H,7.50; N, 10.21 Found: C,60.87; H,7.67; N,9.80.

(2) The method used was that described for the above run except that 1.67 g. (2.6 mmole) of the product of Example I, 50 ml. of ethyl acetate, and 0.43 g. (3.74 mmole) of 4-methyl-1-aminopiperazine were used. After chromatography (4 × 40 cm. column containing 196 g. of silica gel) eluting with chloroform:methanol:benzene (8:1:1), 0.90 g. of product (51%) was collected and had the same physico-chemical characteristics as those reported in the first run.

4-Methyl-1-aminopiperazine for use in the above example was prepared as follows. Dinitrogen trioxide was bubbled into a stirred solution of 20.0 g. of N-methylpiperazine in 100 ml. of water at such a rate that the temperature was maintained at 10° C. with the aid of an ice-water bath. After the solution turned yellow nitrosation was stopped and the nitroso compound was salted out using potassium carbonate in slight excess. The mixture was extracted with three 100-ml. portions of ether and concentrated, and the residue was distilled at 77°-78° C. to give 23.4 g. (90%) of 1-nitroso-4-methylpiperazine. Reduction of the nitroso compound using 10.0 g. of lithium aluminum hydride in 200 ml. of ether gave 18.7 g. (90%) of 1-amino-4-methylpiperazine, b.p. 171°-173° C.

EXAMPLE III (1) A mixture of 0.336 g. (0.52 mmole) of the product of Example I, 20 ml. of dry ethyl acetate and 0.164 g. (0.74 mmole) of O-benzhydrylhydroxylamine hydrochloride was stirred for 20 hours at 50°-55° C., then evaporated to dryness. The crude product was dissolved in a small amount of acetone and chromatographed on a silica gel column (2 cm. × 45 cm.) with chloroform:methanol:benzene (8:1:1). After isolation of the orange-brown fraction from the column and filtration, solvent was evaporated to dryness, to yield 0.217 g. of product (54%), m.p. 205°-207° C.

Analysis calcd. for $C_{43}H_{51}O_{10}N_3$: C,67.08; H,6.68; N,5.46 Found: C,67.08; H,6.86; N,5.65;

(2) The same method was used as described for the first run, but 1.37 g. (2.13 mmole) of the product of Example I, 80 ml. of dry ethyl acetate, and 0.68 g. (3.1 mmole) of O-benzhydrylhydroxylamine hydrochloride were employed. Chromatography employing a 4 cm. × 40 cm. column, containing 196 g. of silica gel and chloroform:methanol:benzene (8:1:1) as solvent gave 0.7 g. (37%) of product with the same physico-chemical characteristics as in the first run.

EXAMPLE IV (1) A mixture of 0.167 g. (0.26 mmole) of the product of Example I, 10 ml. of dry ethyl acetate, and 0.068 g. (0.374 mmole) of O-n-octylhydroxylamine hydrochloride was stirred for 20 hours at 55° C. The solvent was evaporated to dryness and the crude residue was chromatographed on a silica-gel plate with chloroform:methanol:benzene (8:1:1). The large orange-brown spot was dried under vacuum at 40° C. for 5 hours to yield 0.084 g. of product (45%) m.p. 65°-67° C.

Analysis calcd. for $C_{38}H_{57}O_{10}N_3$: C,63.75; H,8.02; N,5.87 Found: C,64.04; H,8.25; N,5.98.

(2) The same method was used as in the first run, but 1.67 g. of the product of Example I (2.6 mmole), 80 ml. of dry ethyl acetate, and 0.68 g. (3.74 mmole) of O-n-octylhydroxylamine hydrochloride were used. Column chromatography (4 cm. × 40 cm. column containing 196 g. of silica gel) with chloroform:methanol:benzene (8:1:1) solvent gave 0.86 g. of product (45%), with the same physico-chemical characteristics as reported for the first run.

EXAMPLE V (1) A mixture of 0.167 g. (0.26 mmole) of the product of Example I, 5 ml. of dry ethyl acetate, and 0.0715 g. (0.374 mmole) of 4-benzyl-1-aminopiperazine was agitated for 4 hours at 55° C., then evaporated to dryness. The crude residue was dissolved in a small amount of acetone and chromatographed on a silica gel plate with chloroform:methanol:benzene (8:1:1). The large purple spot was scraped from the plate and eluted from the silica gel with acetone, solvent was evaporated and the product, which contained a small amount of starting material, was chromatographed in chloroform:amyl alcohol (9:1). After isolation of the large purple spot from the plate and filtration, the solvent was evaporated to dryness to yield, 0.084 g. of product (43%), m.p. 134°-136° C.

Analysis calcd. for $C_{41}H_{55}N_5O_9$: C,64.63; H,7.27; N,9.19 Found: C,64.49; H,7.58; N,9.06.

(2) The same method was used as in the first run, but using 1.67 g. (2.6 mmole) of the product of Example I, 50 ml. of dry ethyl acetate, and 0.715 g. (3.74 mmole) of 4-benzyl-1-aminopiperazine. After two column chromatographs over a column 4 × 40 cm. (196 g. silica gel) employing chloroform:methanol:benzene (8:1:1) and chloroform:amylalcohol (9:1), 0.85 g. of product (43%) was obtained having the same physico-chemical characteristics as those reported above.

4-Benzyl-1-aminopiperazine for use in the above example may be prepared as follows.

7.0 g. of N-benzylpiperazine [according to the method of Craig and Young, *Org. Synthesis,* 42, 19 (1962)] was nitrosated by standard procedures to yield 8.2 g. of 1-nitroso-4-benzylpiperazine, b.p. 133°-135° C. The nitroso compound was reduced with lithium aluminum hydride to give 7.6 g. of the desired product, m.p. 124°-125° C.

EXAMPLE VI (1) A mixture of 0.167 g. (0.26 mmole) of the product of Example I, 10 ml. of dry ethyl acetate and 0.06 g. (0.376 mmole) of O-benzylhydroxylamine hydrochloride was stirred for 20 hours at 55°-60° C., then evaporated to dryness. The crude product was dissolved in a small amount of acetone and chromatographed on a silica gel plate with chloroform:methanol:benzene (8:1:1). The large orange-brown spot was scraped from the plate and eluted with acetone. The solvent was evaporated to dryness to yield 0.065 g. of product (36%), m.p. 105°-107° C.

Analysis calcd. for $C_{37}H_{47}N_3O_{10}$: C,64.05; H,6.83; N,6.06 Found: C,63.86; H,7.09; N,5.99

(2) The same method was used as in the first run, but using 1.67 g. (2.6 mmole) of the product of Example I, 80 ml. of dry ethyl acetate, and 0.6 g. (3.76 mmole) of O-benzylhydroxylamine hydrochloride. After column chromatography over a column 4 × 40 cm. (containing 196 g. of silica gel) employing chloroform:methanol:benzene (8:1:1), 0.67 g. (37%) of the product was obtained having the same physico-chemical characteristics as those reported for the first run.

FIG. 1, below illustrates the compounds of Examples I through VI.

FIGURE 1

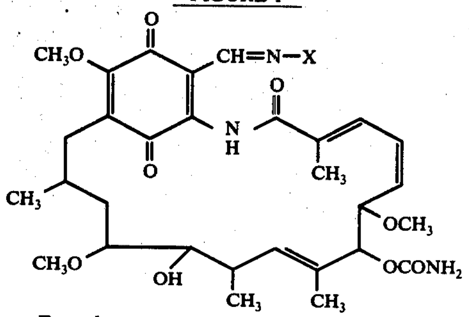

| Example | Identitiy of "X" |
|---|---|
| I | $-C(CH_3)_3$ |
| II | 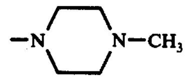 |
| III | $-O-CH(C_6H_5)_2$ |
| IV | $-O-(CH_2)_7CH_3$ |
| V | 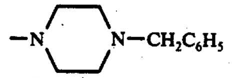 |
| VI | $-O-CH_2C_6H_5$ |

Tables 1, 2 and 3, below, respectively relate to the activity of the compounds of Examples I through V s antibacterial agents, as bacterial RNA polymerase activity inhibitors, and as inhibitors of reverse transcriptase.

Table 1

| | Bacterial Inhibition | | | | |
|---|---|---|---|---|---|
| | MIC[a] (μg/ml) for Example No. | | | | |
| Organism | I | II | III | IV | V |
| *S. Hemolyticus* | 250 | 500 | 31.2 | 7.8 | 125 |
| *St. Faecalis* | >500 | >500 | >500 | >500 | 500 |
| *E. coli* | 500 | 500 | >500 | >500 | 500 |
| *P. vulgaris* | 500 | 500 | >500 | >500 | 500 |
| *K. pneumoniae* | 500 | 500 | >500 | >500 | 500 |
| *Ps. aeruginosa* | 250 | 250 | >500 | >500 | 250 |
| *D. penumoniae* | 250 | 500 | 62.5 | 7.8 | 62.5 |
| *S. aureus* | 500 | >500 | >500 | >500 | 500 |

[a]Minimal inhibitory concentration in brain heart infusion broth.

Table 2

| *E. coli* RNA Polymerase Inhibition | |
|---|---|
| Example No. | % of Control |
| Control | 100 |
| I | 99 |
| II | 106 |
| III | 84 |
| IV | 110 |
| V | 88 |

The assay mixtures contained, in a total volume of 0.25 ml: (Tris)HCl buffer, pH 7.9, 5 μmoles; $MgCl_2$, 1 μmole; mercaptoethanol, 3 μmoles; $MpCl_2$, 0.25 μmole: GTP, UTP, and CTP, 0.1 μmole each; ATP-14C, 0.1 μmole, 0.05 μCi;dAT, 0.07 $OD_{260}$ units; polymerase, 0.5 units; and 0.5 μM/ml of compound. Reactions were run at room temperature for 15 minutes.

Table 3

| Inhibition of Reverse Transcriptase of Rauscher Leukemia Virus | | |
|---|---|---|
| Example No. | cpm* | % Inhibition |
| Control | 5396 | 0 |
| I | 376 | 93.0 |
| II | 357 | 93.4 |
| III | 75 | 98.6 |
| IV | 303 | 94.4 |
| V | 154 | 97.1 |

*(The reverse transcriptase activity was measured at 37° C. for 90 minutes).

The following examples illustrate exemplary procedures for preparation of compounds of Formula II. As indicated supra, compounds of Formula II may be prepared either through direct reaction of geldanamycin with a selected O-phenylenediamine or through reaction of such an amine with an intermediate compound — the product of the reaction of geldanamycin and a suitable hydroxide. The intermediate compound (hereinafter, des-O-methylgeldanamycin) may be prepared according to the following example.

EXAMPLE VII

Des-O-methylgeldanamycin

A solution of 560 mg. of geldanamycin in 15 ml. of tetrahydrofuran was stirred magnetically in a three-necked flask provided with a reflux condenser, while 157.7 mg. of barium hydroxide octahydrate in 15 ml. of water was added dropwise. The solution, which immediately darkened, was heated at 70° C. in an oil bath for 34 hours. The solvent was removed in vacuo and the residue was acidified with 1 N hydrochloric acid. The aqueous layer was extracted with ethyl acetate and the extracts were dried over magnesium sulfate. The solution was filtered through a sintered-glass funnel and the solvent was removed at reduced pressure. The dark residue was dissolved in chloroform and eluted from a 200 g. column of silica gel with 5–10% methanol in chloroform, giving 320 mg. (59%) of product which eluted as a very polar, purple band. Crystallization from benzenemethanol gave yellow needles, m.p. 283° C. NMR, IR, UV and mass spectra confirmed the proposed structure.

Analysis calcd for $C_{28}H_{38}N_2O_9$: C,61.53; H,7.01; N,5.12. Found: C,61.69; H,7.09; N,5.08.

EXAMPLE VIII (1) A mixture of 120 mg. of des-O-methylgeldanamycin, 10 ml. of glacial acetic acid, and 23.7 mg. of freshly crystallized o-phenylenediamine was stirred magnetically at 80° C. for 1.25 hours, then cooled and stirred at room temperature overnight. The solvent was removed in vacuo and the residue was eluted from a 200 g. column of silica gel with 2% methanol in chloroform. The product migrated as a polar red band, yielding 83 mg. (62.7%). Crystallization from chloroform-cyclohexane gave purple needles, m.p. 190°-193° C. The NMR, IR, UV and mass spectra confirmed the proposed structures.

Analysis calcd for $C_{34}H_{42}N_2O_7$: C,66.00; H,6.84; N,9.06 Found: C, 65.51; H,7.01; N,8.63.

(2) Freshly crystallized o-phenylenediamine (108 mg.) was added to a mechanically stirred solution of 560 mg. of geldanamycin in 40 ml. of glacial acetic acid. The mixture was stirred at 80° C. for 30 hours. The acetic acid was removed in vacuo and the residue was chromatographed as described above. Crystallization from chloroformbenzene gave 85 mg. (14%) of product.

The product of the above example has been named demethoxygeldanazine.

EXAMPLE IX

A solution of 304 mg. of 4-methyl-o-phenylenediamine in 10 ml. of glacial acetic acid was added to a magnetically stirred solution of 240 mg. of des-O-methylgeldanamycin in a single-necked flask. A reflux condenser and drying tube were attached to the flask and the mixture was stirred at 84° C. for 1 hour, then at room temperature for 12 hours. The solvent was removed in vacuo and the residue was chromatographed over 100 g. of silica gel with 2% methanol in chloroform. Preparative thin layer chromatography of fractions containing the red band gave 172 mg. (62%) of product, (which was precipitated from a chloroform solution by additon of cyclohexane) m.p. 194° C. The NMR, IR, UV and mass spectra confirmed the proposed structure.

Analysis calcd for $C_{35}H_{44}N_4O_7$: Mol. Wt., 632,3210. Found: Mol. wt., 632.3221 (high resolution mass spec).

EXAMPLE X

A mixture of 120 mg. of des-O-methylgeldanamycin, 10 ml. of glacial acetic acid, and 53 mg. of 3-methyl-o-phenylenediamine was stirred at 75°-80° C. for 1 hour. The mixture was cooled and stirred at room temperature for one hour, then evaporated to dryness in vacuo. The dark residue was chromatographed over 30 g. of silica gel with 2% methanol in chloroform. Preparative thin layer chromotography of the polar red band gave 40 mg. (28%) of dark purple needles, dec. 193°-196° C. The NMR, IR, UV and mass spectra confirmed the proposed structure.

Analysis calcd for $C_{35}H_{44}N_4O_7$: Mol. wt., 632.3210. Found: 632.3197 (high resolution mass spec).

FIG. 2, below, illustrates the compounds of Examples VIII through X.

FIGURE 2

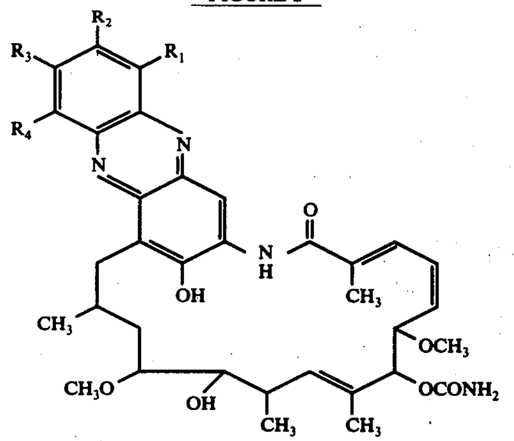

| Example | Identity of $R_1$, $R_2$, $R_3$ and $R_4$ |
|---|---|
| VIII | $R_1 = R_2 = R_3 = R_4 = H$ |
| IX | $R_1 = R_4 = H$, $R_2$ or $R_3 = CH_3$, $R_3$ or $R_2 = H$ |
| X | $R_1 = R_4 = CH_3$, $R_2$ or $R_3 = H$, $R_3$ or $R_2 = CH_3$ |

The following examples illustrate exemplary procedures for the preparation of compounds of Formula III. As in the case of preparation of compounds of Formula II, des-O-methylgeldanamycin may be employed in some preparations.

EXAMPLE XI (1) Freshly sublimed o-aminophenol (55 mg.) was added to a magnetically stirred solution of 273 mg. of des-O-methylgeldanamycin in 20 ml. of glacial acetic acid. The mixture was stirred at 80° C. for 1 hour, then stirred overnight at room temperature. The solvent was removed in vacuo and the residue was eluted from 200 g. of silica gel with chloroform. The phenoxazone eluted first as an orange band which was contaminated with some starting material. Crystallization from chloroform-benzene gave 74 mg. (24%) of yellow needles, m.p. 282°–284.5° C. The NMR, IR, UV and mass spectra confirmed the proposed structures.

Analysis calcd for $C_{34}H_{41}N_3O_8$: C,65.90; H,6.67; N,6.78 Found: C,65.25; H,6.61; N,6.68.

(2) Freshly sublime o-aminophenol (436 mg.) was added to a mechanically stirred solution of 560 mg. of geldanamycin in 74 ml. of glacial acetic acid. The mixture was stirred at 88° C. for 18 hours and the solvent was removed in vacuo. Purification was effected as described above. The yield was 288 mg. (47%) of product which had identical properties as the product obtained in the immediately proceeding preparation.

EXAMPLE XII

A mixture of 612 mg. of 4-methyl-2-nitrophenol, 12 ml. of glacial acetic acid, and 61 mg. of platinum oxide was stirred under hydrogen gas at 1 atmosphere until consumption of hydrogen ceased. The solution was filtered through a sintered-glass funnel and the filtrate was added to a mechanically stirred solution of 560 mg. of geldanamycin in 30 ml. of glacial acetic acid. The mixture was stirred at 84° C. for 1 hour, then stirred at room temperature for 12 hours. The solvent was removed in vacuo and the residue was chromatographed over 100 g. of aluminum oxide with chloroform. The fractions containing the bright orange band were combined and evaporated to dryness at reduced pressure. The orange residue was chromatographed over 30 g. of silica gel with 2% methanol in chloroform to give 117 mg. (19%) of an orange powder product, m.p. 291.5°–294° C. The NMR, IR, UV and mass spectra confirmed the proposed structure.

Analysis calcd for $C_{35}H_{43}N_3O_8$: C,66.33; H,6.84; N,6.63 Found: C,66.10; H,7.01; N,6.51.

EXAMPLE XIII

A mixture of 221 mg. of 2-amino-5-methylphenol, 560 mg. of geldanamycin, and 42 ml. of glacial acetic acid was stirred at 83° C. for 4 hours, then stirred at room temperature for 9 hours. The solvent was removed in vacuo and the residue was eluted from 85 g. of silica gel with a 50% mixture of chloroform and carbon tetrachloride. The fractions containing the bright orange band were combined and eluted from 80 g. of aluminum oxide with 2% methanol in chloroform. Evaporation of solvent and drying at 56° C. for 24 hours gave 139 mg. (20%) of orange powder, dec. 281°–283° C. The NMR, IR, UV and mass spectra confirmed the proposed structure.

Analysis calcd for $C_{35}H_{43}N_3O_8$: C,66.33; H,6.84; N,6.63. Found: C,66.04; H,6.74; N,6.57.

EXAMPLE XIV

A mixture of 459 mg. of 2-methyl-6-nitrophenol, 20 ml. of glacial acetic acid, and 46 mg. of platinum oxide was stirred under hydrogen gas at one atmosphere until consumption of hydrogen ceased. The solution was filtered through a sintered-glass funnel and the filtrate was added to a solution of 560 mg. of geldanamycin in glacial acetic acid. The mixture was stirred at 84° C. for 7 hours and the solvent was removed in vacuo. The dark residue was eluted from 180 g. of aluminum oxide with chloroform and the fractions containing the bright orange band were combined. Chromatography over 80 g. of silica gel with 1% methanol in methylene chloride and crystallization from methylene chloride-benzene gave 281 mg. (45%) of bright orange needles, m.p. 283°–286° C. The NMR, IR, UV and mass spectra confirmed the proposed structure. Analysis calcd for $C_{35}H_{43}N_3O_8$: Mol. wt. 633.3049. Found: Mol. wt. 633.3094 (high resolution mass spec).

EXAMPLE XV

A mixture of 1.744 g. of 4-bromo-2-nitrophenol, 30 ml. of glacial acetic acid, and 170 mg. of platinum oxide was stirred under hydrogen gas at one atmosphere until consumption of hydrogen ceased. The suspension was filtered and the filtrate was added to a solution of 1.2 g. of geldanamycin in 44 ml. of glacial acetic acid. The mixture was stirred at 88° C. for 7 hours and stirred at room temperature for 12 hours. The solvent was removed at reduced pressure and the residue was chromatographed over 150 g. of silica gel with 1% methanol in chloroform. The fractions containing the orange band were combined and evaporated to dryness in vacuo. The residue was chromatographed over 80 g. of aluminum oxide with chloroform and solvent was removed at reduced pressure. Crystallizaton of the orange residue from chloroform gave 160 mg. (12%) of orange needles, dec. 279°–281.5° C. The NMR, IR, UV and mass spectra confirmed the proposed structures.

Analysis calcd for $C_{34}H_{40}BrN_3O_8$: C,58.45; H,5.73; Br,11.46; N,6.02. Found: C,58.03; H,5.85; Br,11.97; N,6.18.

EXAMPLE XVI

A solution containing an excess of 2-amino-4-chlorophenol in 100 ml. of glacial acetic acid was added to a suspension of 9.7 g. of geldanamycin and 100 ml. of glacial acetic acid. The mixture was stirred at 98° C. for 24 hours and the solvent was removed in vacuo. A crude purification of the residue was obtained by rapid chromatography over a 200 g. bed of silica gel in a 200 ml. sintered-glass funnel with 1% methanol in chloroform. The fractions containing the orange band were combined and chromatographed over a mixed column of 450 g. of alumina (lower part of column) and 150 g. of silica gel with 1–2% methanol in methylene chloride. Crystallization from chloroform-diethyl ether gave 1.6 g. (14%) of orange needles, m.p. 277°–279° C. The NMR, IR, UV and mass spectra confirmed the proposed structure.

Analysis calcd for $C_{34}H_{40}ClN_3O_8$: C,62.42; H,6,18; Cl,5.42; N,6.42. Found: C,62.04; H,6.39; Cl,5.41; N,6.44.

EXAMPLE XVII

A mixture of 1.071 g. of 3-hydroxyanthranilic acid hydrochloride in 100 ml. of absolute methanol was methylated with diazomethane in diethyl ether and the solvent was removed in vacuo. The residue was dissolved in 4 ml. of glacial acetic acid and treated immediately with 560 mg. of geldanamycin in 36 ml. of glacial acetic acid. The mixture was stirred at 81° C. for 45 hours and the solvent was removed in vacuo. The residue was dissolved in chloroform and eluted from a 200 g. column of silica gel with 10% ethanol in chloroform. The fractions containing the orange band were combined and chromatographed over a 100 g. column of aluminum oxide with chloroform to give 223 mg. (33%) of orange solid, m.p. 274°–276° C. The NMR, IR, UV, and mass spectra confirmed the proposed structure.

Analysis Calcd. for $C_{36}H_{43}N_3O_{10}$: C,63.80; H,6.40; N,6.20. Found: C,63.95; H,6.44; N,6.08.

EXAMPLE XVIII

A mixture of 199 mg. of N-[3-benzyloxy-4-methyl-2-nitrobenzoyl]-L-threonine methyl ester, 10 ml. of glacial acetic acid, and 20 mg. of 10% palladium on carbon was stirred under hydrogen at one atmosphere until consumption of hydrogen ceased. The suspension was filtered and the filtrate was added to a mixture of 140 mg. of geldanamycin in 10 ml. of glacial acetic acid. The mixture was stirred and heated at 83° C. for 36 hours. The solvent was removed in vacuo and the residue was chromatographed over 50 g. of silica gel with chloroform. The fractions containing the orange band were combined and the solvent was removed at reduced pressure. Preparative thin layer chromatography of the residue on silica gel with 20–30% acetone in benzene gave 62 mg. (16%) of product, dec. 285°-288° C. The IR and mass spectra confirmed the proposed structure.

Analysis Calcd. for $C_{41}H_{52}N_4O_{12}$: Mol wet. 792.3581. Found: Mol wt. 792.3600 (high resolution mass spectrum).

FIG. 3, below, illustrates the structure of the compounds of Examples XI through XVIII.

FIGURE 3

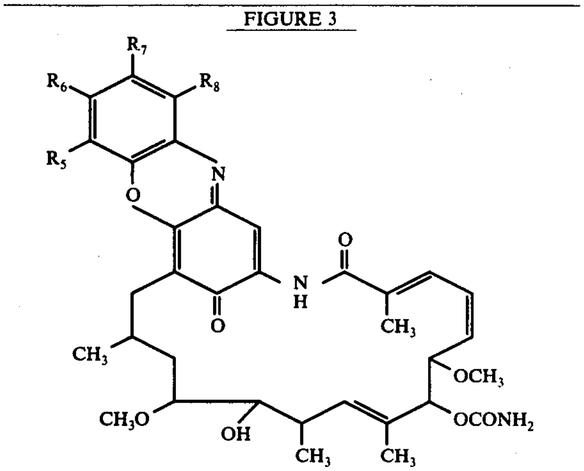

| Example | Indentities of $R_5$, $R_6$, $R_7$ and $R_8$ |
|---|---|
| XI | $R_5 = R_6 = R_7 = R_8 = H$ |
| XII | $R_5 = R_6 = R_8 = H, R_7 = CH_3$ |
| XIII | $R_5 = R_7 = R_8 = H, R_6 = CH_3$ |
| XIV | $R_6 = R_7 = R_8 = H, R_5 = CH_3$ |
| XV | $R_5 = R_6 = R_8 = H, R_7 = Br$ |
| XVI | $R_5 = R_6 = R_8 = H, R_7 = Cl$ |
| XVII | $R_5 = R_6 = R_7 = H, R_8 = CO_2CH_3$ |
| XVIII | $R_5 = CH_3, R_6 = R_7 = H$<br>$R_8 = CO{-}NH{-}CH(COOCH_3){-}CHOH{-}CH_3$ |

Table 4, below, relates to the activity of compounds of Examples VIII through XVIII as bacterial RNA polymerase inhibitors and as inhibitors of reverse transcriptase when tested in the manner the compounds of Examples I through V as related, supra, in Tables 2 and 3.

TABLE 4

| Compound Example No. | *E Coli* RNA Polymerase % Inhibition* | RLV Reverse Transcriptase % Inhibition** |
|---|---|---|
| VIII | 5 - 16 | 98 |
| IX | 16 | 72 |
| X | 12 | 65 |
| XI | 61 - 67 | 98 |
| XII | 9 | 89 |
| XIII | 21 | 77 |
| XIV | 6 | 72 |
| XV | 60 | 82 - 100 |
| XVI | — | 60 |
| XVII | — | 0 |
| XVIII | — | 0 |

*At a concentration of 0.5 μmole/ml.
**At a concentration of 0.25 μmole/ml.

Pharmaceutical compositions of the present invention comprise a minor proportion of one of the compounds of Formulas I, II, and III and a major proportion of a carrier or diluent. The nature of the composition and the carrier or diluent will, of course, depend on the desired route of administration, i.e., orally or parenterally.

Thus, for example, antibacterial and antiviral pharmaceutical compositions could be prepared in the form of compressed tablets, powders, granules, capsules, aqueous solution suspensions in edible oils, aqueous solutions or other dosage forms which are particularly useful for oral administration. Similarly, liquid preparations or formulations may be employed for parenteral use in a medium including a sterile solvent or a sterile suspending vehicle containing an injectable oil, or water-containing hydrophilic colloids such as sodium carboxymethyl cellulose, methyl cellulose, polyvinylpyrrolidone, gelatine, tragacanth and the like.

Antibacterial and antiviral pharmaceutical compositions might also take the form of topical preparations such as ointments and aerosol sprays. They may also include other therapeutic agents.

In the use of compounds of the present invention for the treatment of diseases of viral origin, contact between the compounds and a tumor may be accomplished by dissolving the compounds in a suitable solvent, e.g., aqeous DMSO, ethanol, methanol, chloroform, acetone, methylene chloride, and ethyl acetate and introducing the solution directly or indirectly into the environment of the disease.

The concentration of the compounds in the environment of the disease may be from 20 mcg./ml. to 400 mcg./ml. with from 20 mcg./ml. to 50 mcg./ml. being preferred.

The amount of the compound to be administered for a given antibacterial activity depends on the species, age, and weight of the host as well as the particular conditions to be treated and the route of administration. In general, the parenteral dose expressed as the total amount of the compound is from about 5 to 50 mg./kg. body weight. An oral dose is from about 1 to 10 times the parenteral dose or from 50 to 500 mg./kg. body weight given 1 to 4 times daily.

The following table indicates dosages, for various species (adult):

| Species | Parenteral (mg./kg./day) | Oral (mg./kg./day) |
|---|---|---|
| Dogs | 5 to 50 | 20 to 500 |
| Cats | 5 to 50 | 20 to 500 |
| Rats | 30 to 100 | 100 to 500 |
| Mice | 30 to 100 | 100 to 500 |
| Human | 5 to 100 | 20 to 500 |

The therapeutic methods of the present invention comprise administration of effective amounts of the above-mentioned pharmaceutical compositions to a host afflicted with a bacterial or viral disease.

As used hereinabove, aklyl shall mean saturated or unsaturated, straight or branched chain, monovalent aliphatic radials having 1 to 20 carbon atoms.

As used hereinabove, cyclic amino shall mean monovalent saturated or unsaturated nitrogen-containing cyclic radicals such as pyridine, piperidine, homopiperidine, morpholine and the like.

The foregoing detailed description has been given for clearness of understanding only, and no unnecessary limitations should be understood therefrom as modifications will be obvious to those skilled in the art.

What is claimed is:

1. A compound of the formula

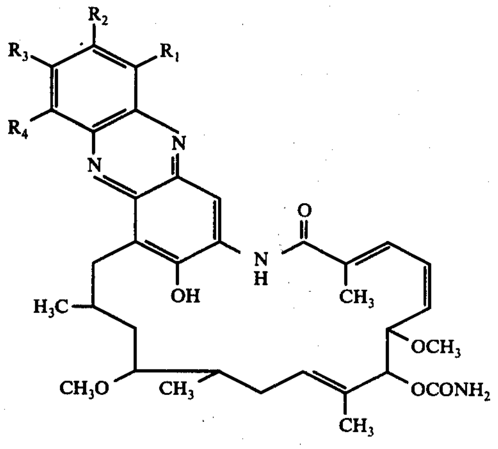

wherein $R_1$, $R_2$, $R_3$, and $R_4$ are the same or different and selected from hydrogen, hydroxy, halo, amino, and $C_1$ to $C_{20}$ saturated alkyl, alkoxy wherein the alkyl portion is $C_1$ to $C_{20}$ saturated alkyl, alkoxycarbonyl wherein the alkyl portion is $C_1$ to $C_{20}$ saturated alkyl, amide or N-alkyl substituted amide wherein the alkyl portion is $C_1$ to $C_{20}$ saturated alkyl.

2. An antibacterial and antiviral pharmaceutical composition comprising a pharmaceutical carrier and from 5 to about 500 mg. of a compound according to claim 1.

3. A therapeutic method for treatment of a host to a bacterial or viral disease which comprises administering a therapeutically effective amount of a compound according to claim 1.

* * * * *

UNITED STATES PATENT OFFICE
CERTIFICATE OF CORRECTION

Patent No. 4,075,339 Dated February 21, 1978

Inventor(s) Kenneth L. Rinehart, Jr., et al.

It is certified that error appears in the above-identified patent and that said Letters Patent are hereby corrected as shown below:

Column 1, line 64, "O-phenylenediamine" should be --o-phenylenediamine--;
line 66, "O-phenylenediamine" should be --o-phenylenediamine--;
Column 2, line 21, "alkoxycarbamyl" should be --alkoxycarbonyl--;
Column 5, line 66, "below" should be --below,--;
Column 6, line 28, "s" should be --as--;
line 53, "$MpCl_2$" should be --$MnCl_2$--;
line 54, "ATP-14C" should be --$ATP^{-14C}$--;
Column 7, line 5, "O-phenylenediamine" should be --o-phenylenediamine--;
Column 8, line 17, "dryiness" should be --dryness--;
Column 9, line 5, "sublime" should be --sublimed--;
Column 12, line 36, "other therapeutic" should be --other compatible therapeutic--;

Signed and Sealed this

*Eleventh* Day of *July 1978*

[SEAL]

*Attest:*

RUTH C. MASON
*Attesting Officer*

DONALD W. BANNER
*Commissioner of Patents and Trademarks*